(12) United States Patent
Richter

(10) Patent No.: US 8,496,703 B2
(45) Date of Patent: *Jul. 30, 2013

(54) AMORPHOUS METAL ALLOY MEDICAL DEVICES

(75) Inventor: Jacob Richter, Arsuf (IL)

(73) Assignee: Zuli Holdings Ltd., Tel Aviv (IL)

( * ) Notice: Subject to any disclaimer, the term of this patent is extended or adjusted under 35 U.S.C. 154(b) by 24 days.

This patent is subject to a terminal disclaimer.

(21) Appl. No.: 13/096,561

(22) Filed: Apr. 28, 2011

(65) Prior Publication Data

US 2011/0202076 A1 Aug. 18, 2011

Related U.S. Application Data

(60) Continuation of application No. 12/243,741, filed on Oct. 1, 2008, now Pat. No. 7,955,387, which is a division of application No. 10/607,604, filed on Jun. 27, 2003, now abandoned.

(51) Int. Cl.
*A61F 2/06* (2006.01)

(52) U.S. Cl.
USPC ..................... 623/11.11; 623/23.53

(58) Field of Classification Search
USPC ............................... 623/1.11–1.48
See application file for complete search history.

(56) References Cited

U.S. PATENT DOCUMENTS

| | | | |
|---|---|---|---|
| 3,986,867 A | 10/1976 | Masumoto et al. | |
| 4,017,911 A | 4/1977 | Kafesjian et al. | |
| 4,142,571 A | 3/1979 | Narasimhan | |
| 4,144,058 A | 3/1979 | Chen et al. | |
| 4,281,706 A | 8/1981 | Liebermann et al. | |
| 4,409,041 A | 10/1983 | Datta et al. | |
| 4,440,585 A | 4/1984 | Kanehira | |
| 4,473,401 A * | 9/1984 | Masumoto et al. | 148/403 |
| 4,481,001 A | 11/1984 | Graham et al. | |
| 4,489,773 A | 12/1984 | Miller | |
| 4,614,221 A | 9/1986 | Masumoto | |
| 4,655,771 A | 4/1987 | Wallsten | |
| 4,802,776 A | 2/1989 | Miyazawa et al. | |
| 5,045,637 A | 9/1991 | Sato et al. | |
| 5,116,360 A * | 5/1992 | Pinchuk et al. | 623/11.11 |
| 5,122,154 A | 6/1992 | Rhodes | |
| 5,368,659 A | 11/1994 | Peker et al. | |
| 5,381,856 A | 1/1995 | Fujikura et al. | |
| 5,393,594 A | 2/1995 | Koyfman et al. | |
| 5,421,919 A | 6/1995 | Roman | |
| 5,464,438 A | 11/1995 | Menaker | |
| 5,514,176 A | 5/1996 | Bosley | |
| 5,562,729 A | 10/1996 | Purdy et al. | |
| 5,591,198 A | 1/1997 | Boyle et al. | |
| 5,636,641 A | 6/1997 | Fariabi | |
| 5,696,207 A | 12/1997 | Vargo et al. | |
| 5,725,573 A | 3/1998 | Dearnaley et al. | |
| 5,788,626 A | 8/1998 | Thompson | |
| 5,797,443 A | 8/1998 | Lin et al. | |
| 5,824,046 A | 10/1998 | Smith et al. | |
| 5,824,052 A | 10/1998 | Khosravi et al. | |
| 5,891,191 A | 4/1999 | Stinson | |
| 5,895,419 A | 4/1999 | Tweden et al. | |
| 5,955,145 A | 9/1999 | Kalvala et al. | |
| 5,964,770 A | 10/1999 | Flomenblit et al. | |
| 6,080,192 A | 6/2000 | Demopulos et al. | |
| 6,096,070 A | 8/2000 | Ragheb et al. | |
| 6,162,537 A | 12/2000 | Martin et al. | |
| 6,187,095 B1 | 2/2001 | Labrecque et al. | |
| 6,190,407 B1 | 2/2001 | Ogle et al. | |
| 6,251,059 B1 | 6/2001 | Apple et al. | |
| 6,287,333 B1 | 9/2001 | Appling et al. | |
| 6,565,507 B2 * | 5/2003 | Kamata et al. | 600/153 |
| 6,610,086 B1 | 8/2003 | Kock et al. | |
| 6,656,218 B1 | 12/2003 | Denardo et al. | |
| 6,733,536 B1 | 5/2004 | Gellman | |
| 6,767,418 B1 | 7/2004 | Zhang et al. | |
| 7,176,344 B2 | 2/2007 | Gustafson et al. | |
| 7,244,116 B2 | 7/2007 | Dubson et al. | |
| 7,329,277 B2 | 2/2008 | Addonizio et al. | |
| 7,360,542 B2 | 4/2008 | Nelson et al. | |
| 7,441,559 B2 | 10/2008 | Nelson et al. | |

(Continued)

FOREIGN PATENT DOCUMENTS

AU 2003-261912 3/2004
EP 0 364 787 A1 4/1990

(Continued)

OTHER PUBLICATIONS

Office Actions and Responses of Related U.S. Appl. No. 11/377,769: Final Rejection dated Jan. 13, 2012.
Office Actions and Responses of Related U.S. Appl. No. 12/428,347: Non-Final Rejection dated Dec. 23, 2011.
Office Actions and Responses of Related U.S. Appl. No. 11/729,516: Final Rejection dated Feb. 1, 2012.
International Search report and Written Opinion dated Aug. 4, 2010 for PCT Application No. PCT/IB2010/001036, 13 pages.
International Search Report and Written Opinion, PCT Application No. PCT/IB04/02096 dated Apr. 5, 2005, 10 pages.
PCT International Search Report, Dec. 8, 2008, 7 pages, from co-pending PCT Application No. PCT/IB2007/000632.

(Continued)

*Primary Examiner* — Suzette J Gherbi
(74) *Attorney, Agent, or Firm* — Cadwalader, Wickersham & Taft LLP

(57) ABSTRACT

This invention provides a new class of medical devices and implants comprising amorphous metal alloys. The medical devices and implants may be temporary or permanent and may comprise other materials as well, such as polymers, ceramics, and conventional crystalline or polycrystalline metal alloys.

Specifically, this invention provides implantable surgical fabrics comprising amorphous metal alloys. The presence of amorphous metal alloys in these fabrics can serve a variety of purposes, including structurally reinforcing the surgical fabric and/or imparting to the fabric the ability to shield against harmful radiation. The fabric may be used inside or outside the body during medical procedures. Further, the implantable surgical fabrics may be woven or non-woven fabrics.

10 Claims, No Drawings

U.S. PATENT DOCUMENTS

| | | | |
|---|---|---|---|
| 7,722,661 B2 | 5/2010 | Lenz et al. | |
| 7,887,584 B2* | 2/2011 | Richter | 623/2.42 |
| 7,955,387 B2* | 6/2011 | Richter | 623/11.11 |
| 2002/0046783 A1 | 4/2002 | Johnson et al. | |
| 2002/0052649 A1 | 5/2002 | Greenhalgh | |
| 2002/0120327 A1 | 8/2002 | Cox et al. | |
| 2002/0161319 A1 | 10/2002 | Matsumoto et al. | |
| 2002/0162605 A1 | 11/2002 | Horton, Jr. et al. | |
| 2003/0040803 A1 | 2/2003 | Rioux et al. | |
| 2003/0050691 A1* | 3/2003 | Shifrin et al. | 623/1.23 |
| 2003/0083646 A1 | 5/2003 | Sirhan et al. | |
| 2003/0120197 A1 | 6/2003 | Kaneko et al. | |
| 2003/0208260 A1 | 11/2003 | Lau et al. | |
| 2003/0211135 A1 | 11/2003 | Greenhalgh et al. | |
| 2004/0072124 A1 | 4/2004 | Kaufman et al. | |
| 2004/0254419 A1 | 12/2004 | Wang et al. | |
| 2004/0255096 A1* | 12/2004 | Norman | 712/11 |
| 2004/0267349 A1 | 12/2004 | Richter | |
| 2005/0033399 A1 | 2/2005 | Richter | |
| 2005/0084407 A1 | 4/2005 | Myrick | |
| 2005/0113888 A1 | 5/2005 | Jimenez et al. | |
| 2005/0216076 A1 | 9/2005 | Kveen et al. | |
| 2005/0261758 A1 | 11/2005 | Rourke et al. | |
| 2006/0149386 A1 | 7/2006 | Clarke et al. | |
| 2006/0178727 A1 | 8/2006 | Richter | |
| 2006/0246210 A1 | 11/2006 | Iki et al. | |
| 2007/0073383 A1 | 3/2007 | Yip et al. | |
| 2007/0219642 A1 | 9/2007 | Richter | |
| 2007/0269936 A1 | 11/2007 | Tanaka et al. | |
| 2008/0097582 A1 | 4/2008 | Shanley et al. | |
| 2008/0319534 A1 | 12/2008 | Birdsall et al. | |
| 2008/0319535 A1 | 12/2008 | Craven et al. | |
| 2009/0012525 A1 | 1/2009 | Buehlmann et al. | |
| 2009/0210049 A1 | 8/2009 | Thielen et al. | |
| 2009/0259294 A1 | 10/2009 | Cully et al. | |
| 2009/0264986 A1 | 10/2009 | Bales et al. | |
| 2010/0004725 A1 | 1/2010 | Zipse et al. | |
| 2010/0070024 A1 | 3/2010 | Venturelli et al. | |
| 2011/0251668 A1 | 10/2011 | Thompson et al. | |

FOREIGN PATENT DOCUMENTS

| | | |
|---|---|---|
| EP | 0 747 498 | 12/1996 |
| EP | 0 775 472 A2 | 5/1997 |
| EP | 03 34 046 B1 | 6/1997 |
| EP | 1 216 717 A1 | 12/2001 |
| EP | 1 937 184 B1 | 8/2006 |
| JP | 61-106133 | 5/1986 |
| JP | 01-121064 | 5/1989 |
| JP | 02-047243 | 2/1990 |
| JP | 02-057264 | 2/1990 |
| JP | 2061036 A | 3/1990 |
| JP | 10-277082 | 7/1990 |
| JP | 07-188876 | 12/1993 |
| JP | 07-080078 | 3/1995 |
| JP | 07-124263 | 5/1995 |
| JP | 07-188877 | 7/1995 |
| JP | 07-265432 | 10/1995 |
| JP | 08-243107 | 9/1996 |
| JP | 2000-167064 | 6/2000 |
| JP | 2000-000297 | 7/2000 |
| JP | 2001-231867 | 8/2001 |
| JP | 2004-089580 | 3/2004 |
| JP | 2007-527734 | 10/2007 |
| WO | WO 83/00997 | 3/1983 |
| WO | WO 95/23876 | 9/1995 |
| WO | WO 00/32138 | 6/2000 |
| WO | WO 01/58504 | 8/2001 |
| WO | WO 02/26279 A1 | 4/2002 |
| WO | WO 02/035984 | 10/2002 |
| WO | WO 2004/016197 | 2/2004 |
| WO | WO 2004/045454 A | 6/2004 |
| WO | WO 2005/000152 | 1/2005 |

OTHER PUBLICATIONS

European Patent Office, Supplementary European Search Report, App. No. EP 04737140, Sep. 5, 2007.

Extended EP Search Report, Application No. EP 09008421.1 dated Jan. 15, 2010.

Extended EP Search Report, Application No. EP 09008420.3 dated Jan. 15, 2010.

Extended EP Search Report, Application No. EP 09008419.5 dated Jan. 15, 2010.

Extended EP Search Report, Application No. EP 07733978.6 dated Mar. 17, 2010.

Horton et al., "Biomedical Potential of a Zirconium-Based Bulk Metallic Glass" Mat. Res. Soc. Symp. Proc. vol. 754, Materials Research Society, Feb. 14, 2003, http://www.ornl.gov/webworks/cppr/y2001/pres/116372.pdf.

Database WPI Week 200012, Derwent Publications, Ltd., London, Great Britain, AN 2000-129595, re JP 2000 000297.

Busch, R1. et al., "On the Glass Forming Ability of Bulk Mettalic Glasses", Materials Science Forum vols. 235-238 (1997) pp. 327-336.

Cahn, R. "Atomic transport in amorphous alloys: An introduction", J. Vac. Sci. Technol. A 4(6), Nov./Dec. 1986.

Metallic Glasses: A New Class of Electroplated Coatings, Suface Finishing, Jul. 1986.

Duwez, P. "A typical example of metastability: Metallic glasses", J. Vac. Sci. Technol. B1 (2) Apr.-Jun. 1987.

Fecht, H. et al., "Destabilization and Vitrification of Crystalline Matter", J. Non-Crystalline Solids, 117/118 (1990) 704-707.

Johnson, W. L. et al. "Electronic Structure of Metallic Glasses", Glassy Metals: Magnetic, Chemical, and Structural Properties, CRC press, pp. 65-108.

Johnson, W. L., "Fundamental Aspects of Bulk Metallic Glass Formation in Multicomponent Assays", Materials Science Form, vols. 225-227 (1996) pp. 35-50.

Johnson, W. L., "Bulk metallic glasses—a new engineering material", Current Opinion in Solid State & Materials Science, 1996, 1:383-386.

Johnson, W. L., "Mechanisms of Instability in Crystalline Alloys With Respect to Vitrification", Journal of Less-Common Metals, 145 (1988) 63-80.

Kavesh, S., "Principles of Fabrication", Metallic Glasses, Papers presented at a Seminar of the Materials Science Division of the American Society for Metals, Sep. 18 and 19, 1976.

Kukulka, D., "New Chill-Block Melt Spinning Relations to Predict Ribbon Thickness", J. Thermophysics, vol. 10, No. 3, Technical Notes, 1996.

Kung, K. T-Y., "Electrical characteristics of amorphous molybdenum-nickel contracts to silicon", J. Appl. Phys., 55(1), May, 15, 1984, pp. 3882-3885.

Liebermann, H. et al., "Technology of amorphous alloys", ChemTech, Jun. 1987, pp. 363-367.

Liebermann, H. H., "The Dependence of the Geometry of Glassy Alloy Ribbons on the Chill Block Melt-Spinning Process Parameters", Materials Science and Engineering, 43 (1980) 203-210.

Takayama S., et al., "The analysis of casting conditions of amorphous alloys", J. Appl. Phys. 50(7), Jul. 1979, pp. 4962-4965.

Thakoor, A. P., et al., "Influence of the microstructure on the corrosion behavior of magnetron sputter-quenched amorphous metal alloys", J. Vac. Sci. Technol. A 1(2), Apr.-Jun. 1983, pp. 520-523.

Williams, R. M. et al., "Corrosion Behavior of Magnetron Sputter-Deposited [Mo0.6Ru0.4]B18 and Mo82B18 Amorphous Metal Films", J. Electrochemical Soc., vol. 131, No. 12, pp. 2791-2794.

Zhu, M. F. et al., "Electrical characteristics of amorphous Ni36W64 contacts on Si", Advanced Semiconductor Processing and Characterization of Electronic and Optical Materials, Proceedings of SPIE, vol. 463, Jan. 24-25, 1984.

Zhu, M. F. et al., "Investigating of Amorphous W60Zr40 Film as a Diffusion Barrier in Metallization Schemes", Phys. Stat. Sol. (a) S6, 471 (1984).

Technology: Hot Alloy [online], Forbes Magazine, Sep. 30, 2002 [retrieved Feb. 19, 2003] Retrieved from the internet: <URL: www.forbes.com/global/2002/0930/128.html>.

Innovative material is stronger than titanium but can be formed like a plastic [online], Jobwerx Manufacturing Network [retrieved Feb. 19, 2003]. Retrieved from the internet: <URL: www.liquidmetal.com/applications/dsp.medical.asp>.

Liquidmetal medical devices [online], Liquidmetal Technologies, [retrieved Feb. 20, 2003]. Retrieved from the internet: <URL: www.liquidmatal.com/applications/dsp.medical.asp>.
Liquidmetal technology reborn in LMG [online], Golfweb, Jul. 31, 2002 [retrieved Feb. 20, 2003] Retrieved from the internet: <URL: www.golfweb.com/u/ce/multi/0,1977m5564401,00.html>.
Choosing the right suture material [online], The Royal College of Surgeons of Edinburgh [retrieved Mar. 5, 2003]. Retrieved from the internet <URL: www.edu.rcsed.ac.uk/lectures/lt5.htm>.
Jostent Peripheral Stent Graft [online]. JOMED 2002 [retrieved Mar. 14, 2003]. Retrieved from the internet: <URL: www.jomed.com/products/jpsg/productinfo/jostent-psg.html>.
Recent Advances in Titanium Wire Technology [online]. TP Orthdontics, Inc. Jan. 1999 [retrieved Mar. 15, 2003]. Retrieved from the internet: <URL: http://www.tportho.com/doctorsroom/whitepapers/pdf/titanium.pdf>.
Lecture 11—Metals for Implantation [online]. Wayne State University [retrieved Mar. 17, 2003]. Retrieved from the internet: <URL: http://ttb.eng.wayne.edu~grimm/BME5370/Lect11Out.html>.
Investment Materials [online]. Guy's, King's College & St. Thomas's Hospital Dental Institute, Dental Biomaterials Science, R.V. Curtis [retrieved Mar. 15, 2003]. Retrieved from the internet: <URL: http://r-curtis.umds.ac.uk/bds3a/investment%20materials%201.htm>.
Metal Casting Alloys [online]. Guy's, King's College & St. Thomas's Hospital Dental Institute, Dental Biomaterials Science, R.V. Curtis [retrieved on Mar. 15, 2003]. Retrieved from the internet: <URL: http://r-curtis.umds.ac.uk/bds3a/BMCalloys.HTM>.
Metals & Alloys [online]. Guy's, King's College & St. Thomas's Hospital Dental Institute, Dental Biomaterials Science, R.V. Curtis, [retrieved on Mar. 15, 2003]. Retrieved from the internet: <URL: http://r-curtis.umds.ac.uk/bds3a/metallurgy.HTM>.
Metallic glasses bulk up, [online]. Mechanical Engineering Magazine, Jun. 1998. [retrieved on Mar. 21, 2003]. Retrieved from the internet: <URL: www.memagazine.org/backissues/june98/features/metallic/metallic.html>.
Hasta La Vista, Titanium, [online]. Business 2.0, Oct. 2002. [retrieved on Mar. 21, 2003]. Retrieved from the internet: <URL: www.business2.com/articles/mag/print/0,1643,43538,00.html>.
New metal alloy is super strong, [online]. You magazine [retrieved on Mar. 21, 2003]. Retrieved from the internet: <URL: www.you.com.au/news/1022.htm>.
Atzmon, M. et al., "Study of Amorphous Phases Formed by Solid-State Reaction in Elemental Composites", Rapidly Quenched Metals, Proceedings of the Fifth International Conference on Rapidly Quenched Metals, Wurzburg, Germany, Sep. 307 [SIC], 1984.
Office Actions and Responses to Office Actions of Related U.S. Appl. No. 10/607,604, now abandoned: Notice of Abandonment dated Jun. 4, 2009; Final Rejection dated Dec. 3, 2008; Amendment and Response to Non-Final Rejection with Extension of Time dated Nov. 13, 2007; Non-Final Rejection dated Jul. 12, 2007; Amendment and Response to Final Rejection with Request for Continued and Extension of Time dated May 2, 2007; Final Rejection dated Nov. 6, 2006; Amendment and Response to Non-Final Rejection with Extension of Time dated Aug. 11, 2006; Non-Final Rejection dated May 1, 2006; Request for continued Examination with Extension of Time dated Apr. 7, 2006; Advisory Action dated Mar. 31, 2006; Amendment and Response to Final Rejection dated Mar. 13, 2006; Final Rejection dated Dec. 12, 2005; Amendment and Response to Non-Final Rejection dated Sep. 15, 2005; Notice regarding Non-Compliant Amendment dated Aug. 24, 2005; Amendment and Reponse to Non-Final Rejection dated May 18, 2005; Non-Final Rejection dated Feb. 23, 2005; Response to Retriction/Election Requirement dated Dec. 17, 2004; and Restriction/Election Requirement dated Nov. 17, 2004.
Office Actions and Responses to Office Actions of Related U.S. Appl. No. 12/243,723 and Patented as 7,887,584: Notice of Allowance and Fees Due dated Nov. 24, 2010; Notice of Allowance and Fees Due dated Oct. 29, 2010; Notice of Allowance and Fees Due dated Oct. 5, 2010; Amendment and Response after Final Rejection with Request for Continued Examination dated Jul. 7, 2010; Examiner Interview Summary dated Jun. 29, 2010; Final Rejection dated Apr. 7, 2010; Amendment and Response to non-Final Rejection dated Dec. 18, 2009; and Non-Final Rejection dated Sep. 18, 2009.
Office Actions and Responses to Office Actions of Related U.S. Appl. No. 12/243,732 now abandoned: Notice of Abandonment dated Oct. 28, 2010; Examiner Interview Summary Record dated Jun. 29, 2010; Final Rejection dated Apr. 9, 2010; Amendment and Response to Non-Final Rejection with Extension of Time dated Jan. 20, 2010; and Non-Final Rejection dated Sep. 21, 2009.
Office Actions and Responses to Office Actions of Related U.S. Appl. No. 12/243,741: Applicant Summary of Interview with Examiner dated Feb. 28, 2011; Notice of Allowance and Fees Due with Examiner Interview Summary Record dated Jan. 28, 2011; Amendment and Response to Non-Final Rejection dated Nov. 29, 2010; and Non-Final Rejection dated Sep. 30, 2010.
Office Actions and Responses to Office Actions of related U.S. Appl. No. 11/377,769: Amendment and Response to Final Rejection with Request for Continued Examination dated Sep. 15, 2010; Final Rejection dated Sep. 15, 2010; Amendment and Response to Non-Final Rejection with Request for Corrected Filing Receipt dated Mar. 24, 2010; Non-Final Rejection dated Dec. 24, 2009; Amendment and Response to Requirement for Restriction/Election dated Sep. 28, 2009; and Requirement for Restriction/Election dated Aug. 27, 2009.
Office Actions and Responses to Office Actions of related U.S. Appl. No. 12/428,347: Non-Final Rejection dated Apr. 27, 2011.
Office Actions and Responses of related U.S. Appl. No. 11/377,769: Amendment and Response to Final Rejection and Request for Continued Examination filed Apr. 13, 2012.
Office Actions and Responses of related U.S. Appl. No. 12/428,347: Supplemental Amendment filed May 9, 2012; and Amendment and Response to Non-Final Rejection with Drawings filed Mar. 22, 2012.
Office actions and responses of related U.S. Appl. No. 12/243,741: Supplemental Notice of Allowability dated May 9, 2011; and Supplemental Notice of Allowability dated Apr. 29, 2011.
Office actions and responses of related U.S. Appl. No. 12/428,347: Examiner Interview Summary dated Jul. 21, 2011; and Non-Final Rejection dated Apr. 27, 2011.
Office actions and responses of related U.S. Appl. No. 11/377,769: Non-Final Rejection dated Aug. 1, 2011.
Extended European Search Report and Opinion from corresponding EP Application No. 12181899.1-2320 dated Oct. 1, 2012, 6 pages.
Extended European Search Report from corresponding EP Application No. 12176459.1-2320, 7 pages.
Extended European Search Report from corresponding EP Application No. 12187494.5-2320 dated Nov. 15, 2012, 6 pages.
Office Action of related U.S. Appl. No. 12/764,418, Non-Final Rejection dated Nov. 28, 2012.
Office Actions and Reponses of Related U.S. Appl. No. 12/428,347 Notice of Allowance dated Oct. 2, 2012.

* cited by examiner

AMORPHOUS METAL ALLOY MEDICAL DEVICES

RELATED APPLICATIONS

This application is a divisional of Ser. No. 10/607,604 filed Jun. 27, 2003. The entirety of this priority application is hereby incorporated in toto by reference.

FIELD OF THE INVENTION

This invention relates to medical devices containing at least one amorphous metal alloy. This invention also relates to temporary and permanent implantable devices that contain at least one amorphous metal alloy.

BACKGROUND OF THE INVENTION

It has become common to treat a variety of medical conditions by introducing an implantable medical device partly or completely into the patient's body. Implantable medical devices are commonplace today in treating cardiac dysfunction, orthopedic conditions, and many other types of conditions requiring surgical intervention. Implantable medical devices fall within two broad categories: permanent and temporary devices. Temporary devices may be later removed from the body or made of bioabsorbable materials that disappear with time without being removed.

Materials used to make both permanent and removable temporary devices often must be made of strong materials which are capable of deforming or bending in accordance with the pressures and movements of the patient's body or the organ in which they are implanted. Current metals have limited fatigue resistance and some suffer from sensitivity to in vivo oxidation. Also, because of the fabrication methods used, many metal devices do not have acceptably smooth, uniform surfaces. This property is important to prevent an adverse response of the device in the body, and to prevent accelerated corrosion of the implanted device. Thus, it is desirable to produce these medical devices with a new material, i.e., one that is non-corrosive, highly elastic, and strong.

One object of the invention relates to producing a medical implant device which is more resistant to repeated deformation when it is used or implanted in the body.

Another object of the invention relates to a medical implant which is corrosion resistant and highly biocompatible.

Yet another object of the invention relates to a medical device which is durable enough to withstand repeated elastic deformation.

SUMMARY OF THE INVENTION

The present invention relates to a medical device containing at least one amorphous metal alloy. Such medical devices provide the advantage of corrosion resistance, resistance to unwanted permanent deformation, and radiation protection. Many medical devices can benefit from such enhanced physical and chemical properties. Implants, radiation shields, surgical devices/materials, dental prostheses, and many other similar devices are a few examples of such medical devices.

In one embodiment, the present invention provides temporary or permanent medical implants comprising at least one amorphous metal alloy. As used herein, an "implant" refers to an article or-device that is placed entirely or partially into an animal, for example by a surgical procedure. This invention contemplates implants that consist of an amorphous metal alloy component (or components) only, as well as implants comprising at least one amorphous metal alloy component combined with components made of other materials, with biocompatible materials being particularly preferred.

The medical devices may contain one or more amorphous metal alloys. Such alloys provide improved tensile strength, elastic deformation properties, and reduced corrosion potential to the devices. Many different types of devices may be formed of or contain amorphous metal alloys. Non-limiting examples include grafts, surgical valves, joints, threads, fabrics, fasteners, sutures, artificial sheets for heart valves, stents and the like.

The medical devices of the present invention are preferably prepared using a process that includes chill block melt spinning. In a preferred embodiment, the chill block melt spinning process comprises the steps of heating an alloy in a reservoir to a temperature 50-100° C. above its melting temperature to form a molten alloy, forcing the molten alloy through an orifice by pressurizing the reservoir to a pressure of about 0.5-2.0 psig, and impinging the molten alloy onto a chill substrate, wherein the surface of the chill substrate moves past the orifice at a speed of between 300-1600 meters/minute.

DETAILED DESCRIPTION OF THE INVENTION

Amorphous metal alloys, also known as metallic glasses, are disordered metal alloys that do not have long-range crystal structure. Many different amorphous metal alloy compositions are known, including binary, ternary, quaternary, and even quinary alloys. Amorphous metal alloys and their properties have been the subject of numerous reviews (see for example, Amorphous Metal Alloys, edited by F. E. Luborsky, Butterworth & Co, 1983, and references therein).

Amorphous metal alloys have been used in the past primarily for items such as computer-related parts, golf club heads, and drill bit coatings. All these are articles made by the so-called bulk process. However, the present invention has recognized that amorphous metal alloys made in a continuous hot extrusion process, as described herein, possess physical and chemical properties which make them attractive candidates for use in medical devices. For example, amorphous metal alloys may have a tensile strength that is up to tenfold higher than that of their conventional crystalline or polycrystalline metal counterparts. Also, amorphous metal alloys may have a tenfold wider elastic range, i.e., range of local strain before permanent deformation occurs. These are important features in medical devices to provide an extended fatigue-resistant lifespan for devices that are subjected to repeated deformations in the body. In addition, these features allow production of smaller or thinner devices that are as strong as their bulkier conventional counterparts.

Many different methods may be employed to form amorphous metal alloys. A preferred method of producing medical devices according to the present invention uses a process generally known as heat extrusion, with the typical product being a continuous article such as a wire or a strip. The process does not involve additives commonly used in the bulk process that can render the amorphous metal alloy non-biocompatible and even toxic. Thus, the process can produce highly biocompatible materials. In preferred embodiments, the continuous amorphous metal alloy articles are fabricated by a type of heat extrusion known in the art as chill block melt spinning. Two common chill block melt spinning techniques that produce amorphous metal alloy articles suitable for the medical devices of the present invention are free jet melt-spinning and planar flow casting. In the free jet process, molten alloy is ejected under gas pressure from a nozzle to form a free melt jet that impinges on a substrate surface. In the planar flow method, the melt ejection crucible is held close to a moving substrate surface, which causes the melt to be in simultaneously in contact with the nozzle and the moving substrate. This entrained melt flow damps perturbations of the melt stream and thereby improves ribbon uniformity. (See e.g., Liebermann, H. et al., "Technology of Amorphous Alloys" Chemtech, June 1987.) Appropriate substrate surfaces for these techniques include the insides of drums or wheels, the outside of wheels, between twin rollers, and on belts, as is well known in the art.

Suitable planar flow casting and free-jet melt spinning methods for producing amorphous metal alloy components for the medical devices of this invention are described in U.S. Pat. Nos. 4,142,571; 4,281,706; 4,489,773, and 5,381,856; all of which are hereby incorporated by reference in their entirety. For example, the planar flow casting process may comprise the steps of heating an alloy in a reservoir to a temperature 50-100° C. above its melting temperature to form a molten alloy, forcing the molten alloy through an orifice by pressurizing the reservoir to a pressure of about 0.5-2.0 psig, and impinging the molten alloy onto a chill substrate, wherein the surface of the chill substrate moves past the orifice at a speed of between 300-1600 meters/minute and is located between 0.03 to 1 millimeter from the orifice. In embodiments involving free jet melt spinning, the process may comprise the steps of heating an alloy in a reservoir to a temperature above the melting point of the alloy, ejecting the molten alloy through an orifice in the reservoir to form a melt stream with a velocity between 1-10 meters/second, and impinging the melt stream onto a chill substrate, wherein a surface of the chill substrate moves past the orifice at a speed of between 12-50 meters/second.

Besides quenching molten metal (e.g., chill block melt spinning), amorphous metal alloys can be formed by sputter-depositing metals onto a substrate, ion-implantation, and solid-phase reaction. Each of these methods has its advantages and disadvantages. The choice of a particular method of fabrication depends on many variables, such as process compatibility and desired end use of the amorphous metal alloy article.

Amorphous metal alloys exhibit significantly different physical properties compared to normal metals, owing to their disordered local microstructure. In contrast to normal metals, which typically contain defects such as grain boundaries and cavities, amorphous metal alloys typically exhibit a uniform random phase on a microscopic scale, and do not contain such defects. As a result, amorphous metal alloys do not experience the strains associated with grain boundaries and/or cavities, and therefore show superior mechanical properties, such as a high elastic modulus, high tensile strength, hardness, and fatigue resistance.

Additionally, many studies have indicated that amorphous metal alloy have superior corrosion resistance compared to their crystalline counterparts. (See Amorphous Metal Alloys, edited by F. E. Luborsky, Butterworth & Co, 1983, p. 479.) In particular, some amorphous metal alloys are known to resist corrosion even by anodic polarization in strongly acidic solutions (e.g., 12 M HCl).

This invention provides a new class of medical devices and implants comprising amorphous metal alloys manufactured by heat extrusion. The amorphous metal alloys contemplated by this invention possess the advantages of almost any desired alloy combination, no toxic additives, and corrosion resistance that results in drastic improvement in bio-compatibility. These amorphous metal alloys have many properties that make them suitable for use as implants, including high mechanical strength, resistance to fatigue, corrosion resistance, and biocompatibility. The implants of this invention may be implanted in animals, non-limiting examples of-which include reptiles, birds, and mammals, with humans being particularly preferred. Besides containing at least one amorphous metal alloy, the implants of this invention may optionally contain other materials, including different types of amorphous metal alloys, conventional crystalline or polycrystalline metals or metal alloys, polymers, ceramics, and natural and synthetic biocompatible materials.

The devices of this invention may be implanted into a body in different ways, including, but not limited to subcutaneous implantation, implantation at the surface of the skin, implantation in the oral cavity, use as sutures and other surgical implantation methods.

The devices may contain one or more amorphous metal alloys. The method of heat extrusion is very flexible and many combinations of metals can be made into an amorphous metal alloy. By way of example, iron-based, cobalt-based alloys, copper-based amorphous metal alloys, as well as others may be manufactured using heat extrusion as described herein. In certain embodiments, the amorphous metal alloys may comprise a metalloid, non-limiting examples of which include silicon, boron, and phosphorus. One possible amorphous metal alloy is an Fe—Cr—B—P alloy. Many other similar alloys are suitable and known to one of ordinary skill in the art.

In certain preferred embodiments, the amorphous metal alloys contemplated by this invention exhibit significantly lower conductance or are non-conductive, compared to their crystalline or polycrystalline counterparts.

In some embodiments of the invention, amorphous metal alloy components for implants may be used, i.e. parts of the implant are made of amorphous metal alloys. These parts may be provided in a variety of ways. For example, the component may be produced by machining or processing amorphous metal alloy stock (e.g., a wire, ribbon, rod, tube, disk, and the like). Amorphous metal alloy stock made by chill block melt spinning can be used for such purposes.

The amorphous metal alloy components of this invention may optionally be combined or assembled with other components, either amorphous metal or otherwise, in order to form the implants of this invention. For example, the amorphous metal alloy components may be combined with a biocompatible polymer or ceramic, a biodegradable polymer, a therapeutic agent (e.g., a healing promoter as described herein) or another metal or metal alloy article (having either a crystalline or amorphous microstructure).

The method of combining or joining the amorphous metal alloy components to other components can be achieved using methods that are well known in the art. Non-limiting examples of joining methods including physical joining (e.g., braiding, weaving, crimping, tying, and press-fitting) and joining by adhesive methods (e.g., gluing, dip coating, and spray coating). Combinations of these methods are also contemplated by this invention.

The implants of this invention may be temporary or permanent medical implants and comprise at least one amorphous metal alloy component. As used herein, an "implant" refers to an article or device that is placed entirely or partially into an animal, for example by a surgical procedure or minimally invasive methods. This invention contemplates both implants that consist of an amorphous metal alloy component (or components) only, as well as implants containing amorphous metal alloy components combined with components made of other materials, with biocompatible materials being preferred. Many different types of implants may be formed of or contain amorphous metal alloys. Non-limiting examples include grafts, surgical valves, joints, threads, fabrics, fasteners, sutures, stents and the like.

One aspect of this invention is to provide an implantable surgical fastener containing at least one amorphous metal alloy. The surgical fastener may be a monofilament or multifilament suture that optionally has a coating, such as a resorbable polymer and/or a healing promoter. The implantable surgical fastener may also be a clamp, clip, sheath, staple, or the like. Other embodiments of surgical fasteners include amorphous metal alloy wires performing as artificial ligaments or tendons.

Another aspect of this invention is to provide a surgical fabric comprising at least one amorphous metal alloy. The fabric may be woven or non-woven. In some embodiments, the surgical fabric is a non-woven fabric which is made of a non-woven polymeric sheet and at least one amorphous metal alloy thread, wire, or foil that is bonded or laminated thereto. In other embodiments, the surgical fabric is a woven fabric containing at least one amorphous metal alloy thread, fiber or foil which may be combined with fibers or threads of another material. The woven fabric may contain a plurality of polymeric threads interwoven with at least one amorphous metal alloy thread. The amorphous metal alloy threads optionally include a coating, such as a polymer coating or a healing promoter.

The surgical fabric of this invention may be implanted into a body as a prosthetic device or a part of a prosthetic device. Alternatively, the surgical fabric may be used outside the body, for example, as a part of a device to shield a patient from radiation.

Yet another aspect of this invention is to provide an artificial heart component, such as an artificial heart valve or a pacemaker, wherein the artificial heart component includes an amorphous metal alloy component. In some embodiments, the artificial heart valve is a ball valve comprising an amorphous metal alloy cage. In other embodiments the artificial heart valve can include leaves made of amorphous metal alloy. The amorphous metal alloy component may also be a sheath or a strut. The pacemaker containing the amorphous metal alloy may house an energy source which is shielded from the body by the amorphous metal alloy.

This invention also provides a stent, graft, or like device wherein the device includes a tube, sheath or coiled wire containing an amorphous metal alloy.

One aspect of this invention is to provide a stent-graft comprising a substantially tubular member containing an amorphous metal alloy and a graft material attached to the substantially tubular member. The graft material optionally comprises a surgical fabric containing an amorphous metal alloy with the advantage of making it stronger or alternatively thinner for a given desired strength than conventional materials.

The present invention also provides orthopedic implant devices containing an amorphous metal alloy components. The implants may be used for reconstructive surgery. In some embodiments, the orthopedic implant may contain wires and sheets to perform as ligaments/tendons, springs, tissue growth limiters and the like.

In other embodiments of this invention, the orthopedic implant is an artificial joint containing an amorphous metal alloy. The artificial joint may be a ball-in-socket joint, knee joint or elbow joint or ligament/tendon replacements in such locations.

Those of ordinary skill in the art will recognize that many types of medical devices, such as, for example, implants or implant components are possible based on the teachings and disclosure of this patent. Accordingly, the following examples are to be viewed as merely illustrative of the concept of the invention, and are by no means limiting.

EXAMPLE 1

Sutures Comprising Amorphous Metal Alloys

This invention provides implants comprising amorphous metal alloys for reconstructive surgery. One aspect of this invention provides surgical fasteners comprising amorphous metal alloy. The term "surgical fastener", as used in this context, refers to an implantable device that can be used to hold tissue in place. Non-limiting examples of such fasteners include clamps, clips, sheaths, sutures, and staples. The surgical fasteners may be temporary (e.g., removable staples that aid in the closing of a surgical incision but are removed when the tissue is healed) or permanent (e.g., a clip fastened to a bone to restore the proper position of a displaced ligament or tendon).

Amorphous metal alloys are suitable because of their high mechanical strength, resistance to in vivo oxidation and corrosion, and overall biocompatibility. The surgical fasteners may be made by heat extrusion methods described above. In certain embodiments, the surgical fastener of this invention consists of an amorphous metal article that can be directly implanted into a living creature. Alternatively, the surgical fastener may be combined with other components such as biodegradable polymers and/or therapeutic agents (e.g., thrombosis or fibrinolytic inhibitors) to promote healing.

In certain embodiments of this invention, the surgical fasteners are sutures. A good suture material must meet demanding mechanical and biological requirements. For example, the tensile strength of a suture material, which is defined as the number of pounds of tension that the suture will withstand before it breaks when knotted or fixed in some other way, must be able to withstand not only the strain caused by the joining of the tissues to be sutured, but also any additional strains caused by the inevitable movement by the patient. This is particularly critical when the suture material is used to suture tissues having a high natural tension, such as fasciae or tendons. In addition to meeting stringent mechanical requirements, a good suture material should be biologically inert and should elicit a minimal tissue reaction from the patient, if at all. Excess tissue reaction is known to promote infection and retard healing.

Suture materials can be classified under various categories. For example, a suture material can be made from a single strand of material ("monofilament") or made from several filaments that are joined together ("multifilament"), typically by methods such as braiding or twisting. Monofilament sutures tie smoothly and are less likely to harbor microorganisms, but can be prone to knot slippage. Multifilament sutures, on the other hand, typically have good handling and tying qualities, but can harbor microorganisms.

This invention provides sutures comprising amorphous metal alloys. The sutures may be monofilament sutures comprising a single strand of amorphous metal alloy filament. In certain embodiments, the monofilament amorphous metal alloy sutures also comprise an additional sheath or coating (e.g., an absorbable polymer coating) which modifies the biological or mechanical properties of the monofilament suture. For example, the coating or sheath may be used to prevent or to reduce knot slippage, to improve the biocompatibility, or to modify the chemical properties of the surface of the suture.

Alternatively, the sutures may be multifilament sutures comprising at least one amorphous metal alloy filament. In certain embodiments, the multifilament sutures comprise at least one amorphous metal alloy filament that is joined (e.g., via braiding or twisting) with polymeric filaments. Such polymeric filaments may be made from inert, non-biodegradable materials or resorbable polymers according to methods that are well known in the art. Alternatively, the multifilament sutures of this invention may be made by braiding or twisting together a plurality of amorphous metal alloy filaments, without any polymeric filaments. As in the case for the monofilament sutures of this invention, the amorphous metal alloy filaments in the multifilament sutures contemplated by this invention optionally may have a coating or sheath to improve or to modify the chemical, biochemical, or mechanical properties of the filaments.

Amorphous metal alloy filaments for such use can be made by heat extrusion methods known in the art and described herein.

The sutures contemplated by this invention may be permanent or temporary sutures. The high strength, resistance to corrosion and fatigue, and overall biocompatibility of amorphous metal alloy filaments make sutures comprising such filaments particularly appropriate for permanent sutures. In particular, the high tensile strength of amorphous metal alloy filaments makes sutures comprising such filaments particularly suitable for permanently joining tissue that is expected to be under constant natural tension, such as tendons or fasciae. The use of such sutures may also be advantageous where the diameter of the thread needs to be as small as possible. However, the use of the sutures of this invention as a temporary post-operative surgical fastener is also contemplated. The sutures of this invention may be used like conventional non-resorbable sutures and removed when the tissue joined by the sutures is sufficiently healed.

EXAMPLE 2

Implantable Surgical Fabrics Comprising Amorphous Metal Alloys

This invention provides implantable surgical fabrics comprising amorphous metal alloys. The presence of amorphous metal alloys in these fabrics can serve a variety of purposes, including structurally reinforcing the surgical fabric and/or imparting to the fabric the ability to shield against harmful radiation. The fabric may be used inside or outside the body during medical procedures (e.g. as a fabric to cover areas of the body of the patient or operators during procedures involving hazardous radiation).

The implantable surgical fabrics contemplated by this invention may be woven or non-woven fabrics. In certain embodiments, the implantable surgical fabrics are woven fabrics comprising both polymeric and amorphous metal alloy threads. The implantable woven surgical fabric may comprise bare amorphous metal alloy threads, or optionally amorphous metal alloy threads that have been treated with a coating material prior to implantation in order to improve biocompatibility and/or to promote healing. For example, the amorphous metal alloy threads may be coated with at least one resorbable polymer material, non-limiting examples of which include polyglycolides, polydioxanones, polyhydroxyalkanoates, polylactides, alginates, collagens, chitosans, polyalkylene oxalate, polyanhydrides, poly(glycolide-co-trimethylene carbonate), polyesteramides, or polydepsipeptides. Alternatively, the coating material may comprise healing promoters such as thrombosis inhibitors, fibrinolytic agents, vasodilator substances, anti-inflammatory agents, cell proliferation inhibitors, and inhibitors of matrix elaboration or expression. Examples of such substances are discussed in U.S. Pat. No. 6,162,537, which is hereby incorporated by reference in its entirety. This invention also contemplates using a polymer coating (e.g., a resorbable polymer) in conjunction with a healing promoter to coat the amorphous metal alloy wires.

The polymeric threads of the woven surgical fabrics contemplated by this invention may be resorbable or completely inert towards biodegradation. When the polymer fibers are resorbable, the in vivo degradation of the fibers leaves behind a woven amorphous metal alloy fabric that reinforces the injured tissue. In some embodiments of this invention, both resorbable and inert polymer threads are woven with the amorphous metal alloy thread. In other embodiments, the polymer threads (resorbable, inert or a combination of both) are joined to an amorphous metal alloy foil, for example, by lamination.

In certain embodiments of this invention, the surgical fabrics comprise amorphous metal alloy threads, but not polymer threads. In these embodiments, the amorphous metal alloy threads may be bare or may be coated as described above.

The surgical fabrics of this invention may also be non-woven. For example, the surgical fabric may comprise at least one fluoropolymer or polyolefin sheet that is reinforced with a plurality of amorphous metal alloy threads, a fine amorphous metal alloy mesh, or an amorphous metal alloy foil. The amorphous metal alloy threads, mesh, or foil may be bonded to one or more fluoropolymer sheets by methods that are well known in the art, such as lamination.

In certain embodiments of the woven and non-woven surgical fabrics of this invention, the amorphous metal alloy threads are added to the fabric in a non-isometric way, causing the fabric to have different mechanical properties in different directions. For example, the amorphous metal alloy threads may be added in one direction, causing the fabric to be stiff in one direction, but soft and extendable in the transverse direction.

The surgical fabrics contemplated by this invention may be used for a variety of purposes. For example, the surgical fabric may be fashioned into a vascular graft, where the presence of reinforcing amorphous metal alloy threads or mesh provides better resistance to the continuous pressure caused by arterial or venous blood flow. The surgical fabrics of this invention may also be used as an endoprosthesis for repairing defects in the abdominal wall of a mammal and for preventing the formation of hernias.

Another use of the surgical fabrics of this invention is as an internal radiation shield. For example, the surgical fabric can be used to encase an energy or radiation emitting power source, such as e.g., a radioactive power source for a medical device (e.g., a pacemaker), so that the tissue surrounding the power source experiences minimal or no damage from the source.

EXAMPLE 3

Stents Comprising Amorphous Metal Alloys

A stent is a tubular implant that is surgically inserted into a body lumen, in order to widen the lumen or to ensure that the lumen remains open. Stents have been used for repairing many body conduits, including those of the vascular, biliary, genitourinary, gastrointestinal, and respiratory systems.

Stents are typically inserted into the patient in an unexpanded form, positioned at the site to be repaired, and then expanded. To make positioning of the stent easier, the radial dimension of the stent in its unexpanded form should be less than that of the body lumen. Additionally, a stent should have longitudinal flexibility so that it can more easily negotiate the typically tortuous path-to the site to be repaired. To fulfill these mechanical requirements, stents may be made of elastic materials such as spring steels, stainless steel, Nitinol, Elgiloy or inelastic materials such as tantalum, titanium, silver and gold.

This invention provides implantable stents comprising at least one amorphous metal alloy. Amorphous metal alloys are particularly suitable stent materials for several reasons. For example, amorphous metal alloys have a wide elastic range which makes them ideal for stents implanted in areas of the body that may be subject to outside forces after implantation. The material may be less traumatic due to its non-conductance (or low conductance) and biocompatibility. Additionally, the high strength of amorphous metal alloys may allow stents to be made of thinner material, further decreasing trauma.

The amorphous metal alloy stents of this invention may be made according to designs that are well known in the art. For example, the stents may comprise amorphous metal alloy wires that are shaped into an expandable cylindrical structure, or etched in different methods from sheets of amorphous metal and then rolled and fastened to make a cylinder, or etched from an amorphous metal tube. The etching in these embodiments, whether flat or tubular may be by chemical etching, EDM, LASER cutting, etc. The fastening of a flat structure to a cylinder may be achieved by methods such as fusing, mechanical locking, and the like.

The amorphous metal alloy stents of this invention may comprise other materials as well. In some embodiments, the stents comprise an additional graft member that comprises a flexible, biocompatible matrix designed to promote incorporation of the stent into the wall of the body lumen at the site to be repaired. The stent, graft, or both may additionally comprise a polymer (e.g., a resorbable polymer) or healing promoters, non-limiting examples of which include thrombosis inhibitors, fibrinolytic agents, vasodilator substances, anti-inflammatory agents, and cell proliferation inhibitors. In certain embodiments, the amorphous metal alloy stent may be directly coated with a polymer and/or a healing promoter. In other embodiments, the graft comprises surgical fabrics containing amorphous metal alloys as disclosed herein. In a preferred embodiment, the surgical fabrics fabricated such that the mechanical properties of the fabric are different in different directions. For example, the graft may be soft and extendable in the longitudinal direction, but very stiff and non-extending in the circumferential direction.

EXAMPLE 4

Artificial Heart Valves Comprising Amorphous Metal Alloys

The design and fabrication of a reliable, permanent artificial heart valve requires the careful selection of materials and the consideration of many different factors. The artificial heart valve must be able to withstand the corrosive environment within the body. This corrosive environment results from the immunogenic response caused by the implanted heart valve as well as by the presence of electrolytes in the bloodstream and surrounding tissue, which can cause metal components in the artificial heart valve to oxidize and/or corrode. The artificial heart valve must also be constructed from a material that can withstand the repeated strain it must undergo during up to 40,000,000 systolic cycles of closing and opening. The position of the valve in the high volume flow of blood transforms the slightest problem in biocompatibility into high probability of valve failure. In addition, very aggressive permanent treatment with blood thinners may become necessary, despite their adverse side effects.

Artificial heart valves comprising hard metals made of fixed leaves that rotate on hinges are known. This structure is suboptimal but no metal is known that will endure the strains existing in natural heart valves. The metal valves also have limited lifetime due to suboptimal biocompatibility leading to thrombosis.

For these reasons, amorphous metal alloys are attractive alternative materials for artificial heart valves. The properties of amorphous metal alloys, such as strain resistance and biocompatibility lead to artificial heart valves with very long lifetimes. This invention provides an artificial heart valve comprising at least one amorphous metal alloy component. Amorphous metal alloy components are particularly suitable for artificial heart valves for several reasons. First, amorphous metal alloys are very biocompatible and corrosion resistant. Second, amorphous metal alloys are resistant to fatigue and creep, due to the absence of defects such as grain boundaries and internal cavities.

This invention contemplates providing amorphous metal alloy components for artificial heart valves, such as cages, flanges, hinges, rings, support struts, and sheaths and springs. The amorphous metal alloy components may be fabricated according to heat extrusion methods, such as chill block melt spinning methods that are well known in the art. Additionally, the amorphous metal alloy components are used in conjunction with other materials, such as biocompatible polymeric or ceramic materials, as is well known in the art.

EXAMPLE 5

Implants Comprising Amorphous Metal Alloys For Reconstructive Surgery

This invention also contemplates orthopedic implants comprising amorphous metal alloys. In some embodiments, the orthopedic implants are in the form of reconstructive hardware for repairing ligaments and tendons. Non-limiting examples of reconstructive hardware include wires, springs, and meshes. The reconstructive hardware may be suitably fabricated from an amorphous metal alloy that exhibits a high fatigue limit, resistance to plastic deformation, good biocompatibility, and resistance to oxidation and corrosion. The reconstructive hardware may be made according to fabrication methods well known in the art, such as heat extrusion and machining.

This invention also provides implantable orthopedic prostheses comprising an amorphous metal alloy. The orthopedic prostheses contemplated by this invention may be an amorphous metal article used alone or in combination with other materials, such as biocompatible polymers or plastics, ceramics, or other biocompatible metals.

This invention also provides tissue growth limiters comprising an amorphous metal alloy. The tissue growth limiter of this invention may comprise other materials, such as biocompatible and/or biosorbable polymers. In some embodiments, the tissue growth limiter is in the form of a sheath comprising amorphous metal alloys. In other embodiments, the tissue growth limiter is a fabric containing amorphous metal alloys, such as the surgical fabrics described herein.

EXAMPLE 6

Orthodontic and Dental Implants Comprising Amorphous Metal Alloys

This invention provides orthodontic implants comprising amorphous metal alloys. The orthodontic implants contemplated by this invention include permanent implants (e.g., tissue growth limiters) as well as temporary implants (e.g., orthodontic wires and braces used in orthodontic braces for realigning teeth).

Orthodontic Wires and Brackets

The wires that are used in orthodontic braces must meet demanding mechanical and chemical requirements. For example, the wire must be able to resist breakage during the initial insertion step when the wire is fastened to a metal band or anchor that is fixed to a tooth. Once in place, the wire must be able to withstand the constant tension set by the orthodontist as well as the repeated mechanical stress caused when the patient eats. Additionally, the wire must not be susceptible to corrosion, even when the patient consumes acidic or salty foods.

Currently, several types of orthodontic wire materials are known. Stainless steel has been the predominant choice for use as wires in most orthodontic braces. However, other metals and metal alloys have found niche applications. For example, wires made of cobalt-chromium alloys can be manufactured to provide variable material stiffness. Additionally, a titanium-molybdenum alloy known as beta-titanium can be used to provide a moderately stiff wire that is more stiff than nickel-titanium wires but less stiff than stainless steel wires.

Some alloys used for orthodontic treatments are known to have certain drawbacks. For example, it has been reported that beta-titanium wires have a tendency to break when they are bent or twisted during clinical treatment. This tendency may result from defects such as microcracks or inclusions. Furthermore, nickel-chromium alloys, while strong even in thin cross-section, can cause abutting teeth to discolor.

This invention provides amorphous metal alloy wires for the controlled movement of teeth using conventional orthodontic braces. Amorphous metal alloy wires are particularly useful because they are highly resistant to fatigue, biocompatible, and corrosion-resistant. Additionally, amorphous metal alloys are known to have a high elastic modulus. Accordingly, because the wires are more resistant to stretching under tension, it is easier to maintain constant tension on the teeth, leading to reduced treatment times.

The amorphous metal alloys wires may be made by techniques well known in the art and are commercially available. The wires can be inserted into conventional orthodontic hardware (e.g., brackets or clamps) in the same manner as the wires that are currently known in the art.

This invention also provides orthodontic brackets and clamps comprising amorphous metal alloys. The brackets may be made according to designs that are well known in the art by methods such as machining. In a preferred embodiment of the invention, the brackets and clamps are used in conjunction with orthodontic wires comprising an amorphous metal alloy as described herein.

Tissue Growth Limiters

This invention provides tissue growth limiters comprising an amorphous metal alloy for oral or orthodontic implants. In some embodiments, the tissue growth limiter exclusively consists of an amorphous metal alloy article, while in other embodiments, an amorphous metal alloy article is combined with other biocompatible and/or biosorbable materials. Non-limiting examples of tissue growth limiters contemplated by this invention include sheaths, meshes, and fabrics, such as the surgical fabrics described herein.

I claim:

1. An implantable surgical fabric comprising a non-woven sheet reinforced with an amorphous metal alloy throughout the surgical fabric, wherein the non-woven sheet comprises a plurality of amorphous metal alloy threads.

2. The implantable surgical fabric according to claim 1, wherein the amorphous metal alloy threads include a coating.

3. The implantable surgical fabric according to claim 2, wherein the coating comprises a polymeric material.

4. The implantable surgical fabric according to claim 3, wherein the polymeric material is a resorbable polymer.

5. The implantable surgical fabric according to claim 4, wherein the resorbable polymer comprises an element selected from the group consisting of polyglycolides, polydioxanones, polyhydroxyalkanoates, polylactides, alginates, collagens, chitosans, polyalkylene oxalate, polyanhydrides, poly(glycolide-co-trimethylene carbonate), polyesteramides, and polydepsipeptides.

6. The implantable surgical fabric according to claim 2, wherein the coating comprises a healing promoter.

7. The implantable surgical fabric according to claim 6, wherein the healing promoter is selected from the group consisting of thrombosis inhibitors, fibrinolytic agents, vasodilator substances, anti-inflammatory agents, cell proliferation inhibitors, inhibitors of matrix elaboration, and inhibitors of matrix expression.

8. The implantable surgical fabric according to claim 2, wherein the coating comprises a polymeric material and a healing promoter.

9. The implantable surgical fabric according to claim 1, wherein said amorphous metal alloy comprises an element selected from the group consisting of silicon, boron, and phosphorous.

10. The implantable surgical fabric according to claim 1, wherein said amorphous metal alloy is an iron-based alloy containing Fe, Cr, B, and P.

* * * * *